US008945846B2

(12) United States Patent
Gotlib et al.

(10) Patent No.: US 8,945,846 B2
(45) Date of Patent: Feb. 3, 2015

(54) MUTATIONS IN THE LNK GENE IN PATIENTS WITH MYELOPROLIFERATIVE NEOPLASMS AND OTHER HEMATOLYMPHOID MALIGNANCIES

(75) Inventors: Jason Robert Gotlib, Palo Alto, CA (US); Garry P. Nolan, San Francisco, CA (US); James L. Zehnder, Menlo Park, CA (US); Stephen Tracy Oh, St. Luis, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 925 days.

(21) Appl. No.: 13/005,455

(22) Filed: Jan. 12, 2011

(65) Prior Publication Data

US 2012/0046233 A1    Feb. 23, 2012

Related U.S. Application Data

(60) Provisional application No. 61/295,117, filed on Jan. 14, 2010.

(51) Int. Cl.
*C12Q 1/68* (2006.01)
*C07H 21/02* (2006.01)
*C07H 21/04* (2006.01)

(52) U.S. Cl.
CPC ........ *C12Q 1/6886* (2013.01); *C12Q 2600/156* (2013.01); *C12Q 2600/136* (2013.01)
USPC ......... 435/6.13; 435/6.1; 435/6.11; 435/6.12; 435/6.17; 536/23.5; 536/24.31

(58) Field of Classification Search
None
See application file for complete search history.

(56) References Cited

FOREIGN PATENT DOCUMENTS

WO     2008/134759     11/2008
WO     WO 2009/103992  *  8/2009

OTHER PUBLICATIONS

Halushka et al. Nature. Jul. 1999. 22: 239-247.*
Mummidi et al. Journal of Biological Chemistry 2000. 275: 18946-18961.*
Ha et al. Am J Hematology. Aug. 2011. 86: 866-868.*
Gudbjartsson et al. Nature Genetics. 2009. 41: 342-347.*
GeneCard for the LNK/SH2B3 gene available via url: < genecards.org/cgi-bin/carddisp.pl?gene=SH2B3>, printed on Jan. 21, 2014.*
Hirschhorn et al. Genetics in Medicine. vol. 4, No. 2, pp. 45-61, Mar. 2002.*
Hattersley et al. The Lancet. 2005. 366: 1315-1323.*
Lucentini et al. The Scientist (2004) vol. 18, p. 20.*
Li et al. J Immunology. 2000. 164: 5199-5206.*
Bersenev; et al., "Lnk controls mouse hematopoietic stem cell self-renewal and quiescence through direct interactions with JAK2", The Journal of Clinical Investigation (2008), 118(8):2832-2844.
Buza-Vidas; et al., "Cytokines regulate postnatal hematopoietic stem cell expansion: opposing roles of thrombopoietin and LNk", Genes & Development (2006), 20:2018-2023.
Gery; et al., "Adaptor protein Lnk negatively regulates the mutant MPL, MPLW515L associated with myeloproliferative disorders", Blood (2007), 110(9)3360-3364.
Gery; et al., "Lnk inhibits myeloproliferative disorder-associated JAK2 mutant, JAK2V617F", Journal of Leukocyte Biology (2009), 85:957-965.
Oh; et al., "Novel mutations in the inhibitory adaptor protein LNK drive JAK-STAT signaling in patients with myeloproliferative neoplams", Blood (2010), 116 (6):988-992.
Takaki; et al., "Enhanced Hematopoiesis by Hematopoietic Progenitor Cells Lacking Intracellular Adaptor Protein, Lnk", J. Exp. Med. (2002), 195(2):151-160.
Takizawa; et al., "Enhanced engraftment of hematopoietic stem/progenitor cells by the transient inhibition of an adaptor protein, Lnk", Blood (2006), 107(7):2968-2975.
Tong; et al., "Lnk inhibits erythropoiesis and Epo-dependent JAK2 activation and downstream signaling pathways", Blood (2005), 105(12):4604-4612.
Tong; et al., "Lnk Inhibits Tpo-mpl Signaling and Tpo-mediated Megakaryocytopoiesis", J. Exp. Med. (2004), 200 (5):569-580.
Velazquez; et al., "Cytokine Signaling and Hematopoietic Homeostasis Are Disrupted in Lnk-deficient Mice", J. Exp. Med. (2002), 195(12):1599-1611.
Gery; et al., "Expression of the adaptor protein Lnk in leukemia cells", Experimental Hematology (May 2009), 37 (5):585-592.
Gery; et al., "Lnk inhibits myeloproliferative disorder-associated JAK2 mutant, JAK2V617F", Journal of Leukocyte Biology (Jun. 2009), 85(6):957-65.
Huang; et al., "Defining the Specificity Space of the Human Src Homology 2 Domain", Molecular & Cellular Proteomics (Apr. 2008), 7(4)768-84.
Lemmon; et al., "Signal-dependent membrane targeting by pleckstrin homology (PH) domains", Biochemical Journal (Aug. 2000), 350 Pt 1:1-18.
Shen; et al., "Conservation and covariance in PH domain sequences: physicochemical profile and information theoretical analysis of XLAcausing mutations in the Btk PH domain", Protein Engineering, Design & Selection (Apr. 2004), 17(3):267-276.

* cited by examiner

*Primary Examiner* — Carla Myers
(74) *Attorney, Agent, or Firm* — James S. Keddie; Makoto Tsunozaki; Bozicevic, Field & Francis LLP

(57) ABSTRACT

Aspects of the present invention include methods, compositions and kits for classifying a subject as having or being predisposed to a hematolymphoid neoplasm or malignancy if they harbor a mutation in the LNK gene. Aspects of the present invention also include screening for candidate agents for treating LNK mutation-based hematolymphoid neoplasms or malignancies in cell-based and cell free assays as well as therapeutic compositions for treating a LNK-mutant based hematolymphoid disorder. Also provided are compositions, systems, kits and computer program products that find use in practicing the subject methods.

3 Claims, 12 Drawing Sheets

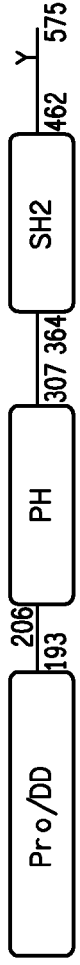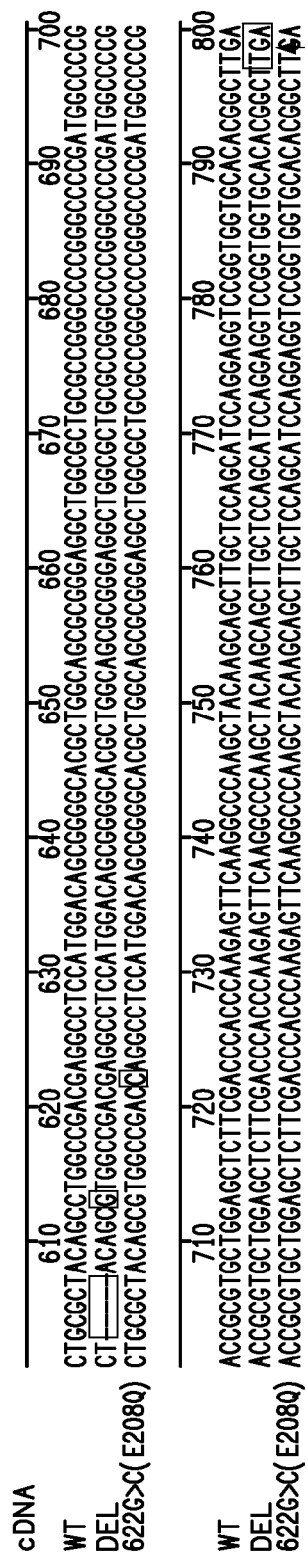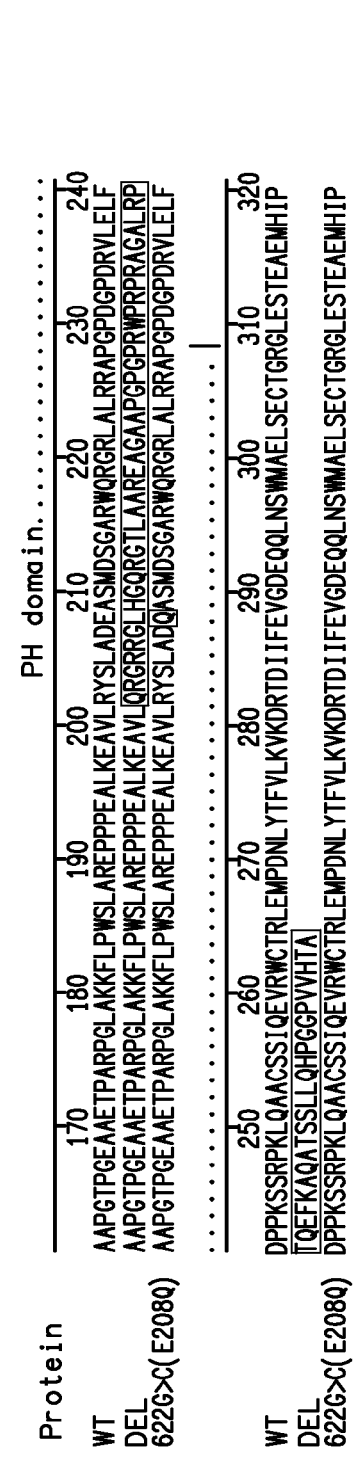

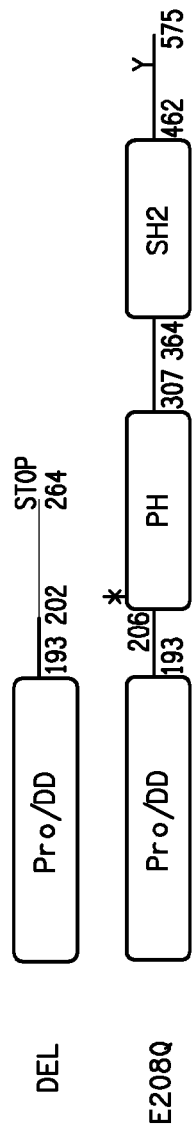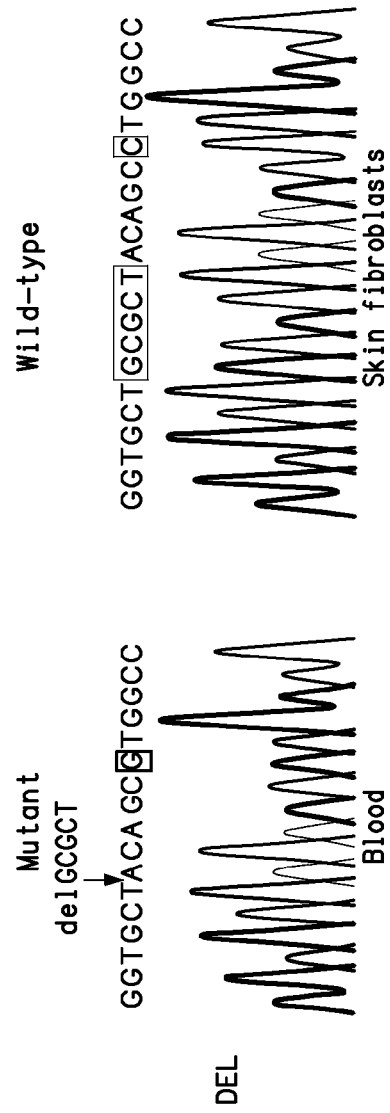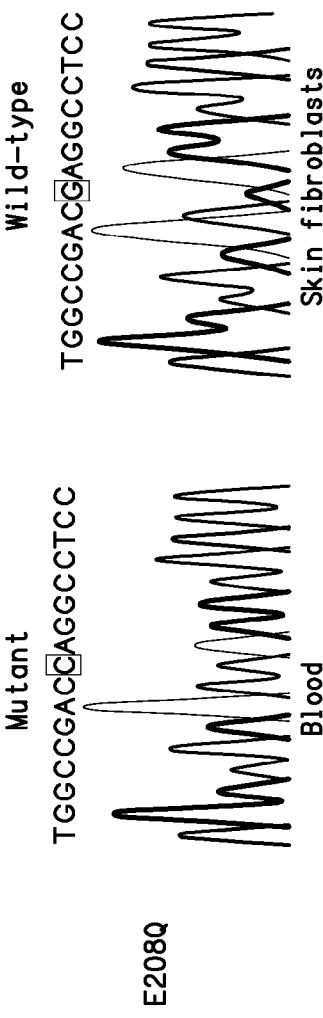
FIG. 1D
FIG. 1E

| | Unsorted | T cells | Granulocytes | Mature monocytes | Immature myeloid | pStat5+ pStat3+ |
|---|---|---|---|---|---|---|
| CD3 | n/a | + | − | − | − | − |
| CD66 | n/a | n/a | + | − | − | − |
| CD33 | n/a | n/a | n/a | + | + | + |
| CD14 | n/a | n/a | n/a | + | − | − |
| pStat5 | n/a | n/a | n/a | n/a | n/a | + |
| pStat3 | n/a | n/a | n/a | n/a | n/a | + |

| Cell line | Timepoint | pJAK2 Fold Chg | pSTAT3 Fold Chg | pSTAT5 Fold Chg |
|---|---|---|---|---|
| EV | 0min | 1.0 | 1.0 | 1.0 |
| | 30min | 3.9 | 2.4 | 5.3 |
| | 60min | 3.8 | 2.6 | 5.4 |
| | 120min | 2.5 | 2.0 | 3.0 |
| | 16hrs | 1.1 | 1.1 | 1.1 |
| WT | 0min | 1.0 | 1.0 | 1.0 |
| | 30min | 2.6 | 1.7 | 3.5 |
| | 60min | 1.9 | 1.5 | 2.4 |
| | 120min | 1.4 | 1.4 | 1.4 |
| | 16hrs | 1.1 | 1.1 | 1.0 |
| DEL | 0min | 1.0 | 1.0 | 1.0 |
| | 30min | 3.9 | 2.4 | 5.2 |
| | 60min | 3.6 | 2.3 | 4.5 |
| | 120min | 2.2 | 2.0 | 2.5 |
| | 16hrs | 1.1 | 1.1 | 1.0 |
| E208Q | 0min | 1.0 | 1.0 | 1.0 |
| | 30min | 2.7 | 1.9 | 4.2 |
| | 60min | 2.0 | 1.5 | 2.6 |
| | 120min | 1.2 | 1.3 | 1.4 |
| | 16hrs | 1.0 | 1.0 | 0.9 |
| R392E | 0min | 1.0 | 1.0 | 1.0 |
| | 30min | 3.7 | 2.4 | 5.1 |
| | 60min | 3.7 | 2.5 | 4.9 |
| | 120min | 3.3 | 2.6 | 4.3 |
| | 16hrs | 1.0 | 1.0 | 0.9 |

*FIG. 4*

MUTATIONS IN THE LNK GENE IN PATIENTS WITH MYELOPROLIFERATIVE NEOPLASMS AND OTHER HEMATOLYMPHOID MALIGNANCIES

CROSS REFERENCE TO RELATED APPLICATION

This application claims priority from U.S. Provisional Application Ser. No. 61/295,117 filed on Jan. 14, 2010, the entirety of which is incorporated herein by reference.

GOVERNMENT RIGHTS

This invention was made with Government support under contracts HV028183 and CA034233 awarded by the National Institutes of Health. The Government has certain rights in this invention.

SUMMARY OF THE INVENTION

Aspects of the present invention include methods, compositions and kits for screening a subject for a hematolymphoid neoplasm or malignancy, or as having a predisposition or higher susceptibility of having a hematolymphoid neoplasm or malignancy, by determining the sequence of the LNK gene, where the presence of a sequence variation as compared to the wild type sequence indicates that the subject has a hematolymphoid neoplasm or malignancy or a predisposition or higher susceptibility of developing a hematolymphoid neoplasm or malignancy. Aspects of the present invention also include screening for candidate agents for treating hematolymphoid neoplasms or malignancies by contacting the candidate agent with a cell comprising an LNK mutant and determining whether the candidate agent Also provided are compositions, systems, kits and computer program products that find use in practicing the subject methods. The methods and compositions find use in a variety of applications.

Aspects of the invention further include methods of characterizing and classifying a hematolymphoid neoplasm or malignancy and determining a therapy dependant upon the type of LNK mutation(s) present.

Aspects of the invention further include mutant LNK gene(s) and expressed mutant protein(s) for drug screening and development, gene therapy and other uses to prevent or amelorate the effects of or resulting from the mutant LNK gene.

DEFINITIONS

For convenience, certain terms employed in the specification, examples, and appended claims are collected here.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

As used herein, the term "gene" or "recombinant gene" refers to a nucleic acid comprising an open reading frame encoding a polypeptide, including exon and (optionally) intron sequences. The term "intron" refers to a DNA sequence present in a given gene that is not translated into protein and is generally found between exons in a DNA molecule. In addition, a gene may optionally include its natural promoter (i.e., the promoter with which the exons and introns of the gene are operably linked in a non-recombinant cell, i.e., a naturally occurring cell), and associated regulatory sequences, and may or may not have sequences upstream of the AUG start site, and may or may not include untranslated leader sequences, signal sequences, downstream untranslated sequences, transcriptional start and stop sequences, polyadenylation signals, translational start and stop sequences, ribosome binding sites, and the like.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eukaryotic mRNA, genomic DNA sequences from viral, procaryotic or eukaryotic DNA, and even synthetic DNA sequences. A transcription termination sequence may be located 3' to the coding sequence.

The terms "reference" and "control" are used interchangeably to refer to a known value or set of known values against which observed data may be compared. As used herein, known means that the value represents an understood parameter, e.g., a wild type sequence of a gene or protein. A reference or control value may be from a single data point or may be a value calculated based on more than one measurement or data point (e.g., wild type consensus sequence). Any convenient reference or control value(s) may be employed in practicing aspects of the subject invention.

The term "nucleic acid" includes DNA, RNA (double-stranded or single stranded), analogs (e.g., PNA or LNA molecules) and derivatives thereof. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "mRNA" means messenger RNA. An "oligonucleotide" generally refers to a nucleotide multimer of about 10 to 100 nucleotides in length, while a "polynucleotide" includes a nucleotide multimer having any number of nucleotides.

The terms "protein", "polypeptide", "peptide" and the like refer to a polymer of amino acids (an amino acid sequence) and does not refer to a specific length of the molecule. This term also refers to or includes any modifications of the polypeptide (e.g., post-translational), such as glycosylations, acetylations, phosphorylations and the like. Included within the definition are, for example, polypeptides containing one or more analogs of an amino acid, polypeptides with substituted linkages, as well as other modifications known in the art, both naturally occurring and non-naturally occurring.

The term "assessing" and "evaluating" are used interchangeably to refer to any form of measurement, and includes determining the identity of an analyte (e.g., its sequence) and/or whether it is present or not. The terms "determining," "measuring," "assessing," and "assaying" are used interchangeably and include both quantitative and qualitative determinations. Assessing may be relative or absolute. "Assessing the presence of" includes determining the amount of or identity of an analyte in a sample, as well as determining whether it is present or absent.

The terms "profile" and "signature" and "result" and "data", and the like, when used to describe peptide level or gene expression level data are used interchangeably (e.g., peptide signature/profile/result/data, gene expression signature/profile/result/data, etc.).

"Mutation" as used herein refers to an altered genetic sequence which results in the gene coding for a non-functioning protein or a protein with substantially reduced or altered function. Generally, a deleterious mutation is associated with pathology or the potential for pathology.

The LNK gene/protein has the following summary information on the NCBI website: GeneID: 10019; Official Symbol: SH2B3; Official Full Name: SH2B adaptor protein 3; Primary source: HGNC: 29605; See related Ensembl: ENSG00000111252, HPRD: 05480, MIM: 605093; Gene type: protein coding; RefSeq status: VALIDATED; Organism: Homo sapiens; Also known as: LNK; SH2B3.

BRIEF DESCRIPTION OF THE FIGURES

FIG. 1. Structure of LNK and location of mutations. Panel A shows the structure of LNK, which includes an N-terminal proline-rich dimerization domain (Pro/DD), a pleckstrin homology (PH) domain, an SH2 domain, and a C-terminal conserved tyrosine residue (Y). In Panel B, the DNA sequences of wild-type (WT; SEQ ID NO 18) and mutant forms of LNK are displayed. Mutations are shaded. DEL (SEQ ID NO: 19) is a 5 by deletion and missense mutation (603_607delGCGCT; 613C>G) that leads to a frameshift and premature stop codon. 622G>C (SEQ ID NO: 20) is a point mutation in the PH domain. Protein sequences of WT (SEQ ID NO: 21) and mutant forms of LNK are displayed in Panel C. Amino acid changes are shaded. The DEL mutation leads to a frameshift at codon 202, followed by 63 nonsense amino acids and a premature stop codon (SEQ ID NO: 22). This results in the absence of the PH and SH2 domains. The 622G>C mutation leads to a glutamic acid to glutamine substitution (E208Q) within the PH domain (SEQ ID NO: 23). In Panel D, WT and mutant forms of LNK are represented schematically. The location of the E208Q mutation is denoted with an asterisk. Sequencing chromatograms are shown in Panel E, demonstrating that the LNK mutations are present in the blood (DEL is SEQ ID NO: 24; E208Q is SEQ ID NO: 26) but not in germline tissue, in this case skin fibroblasts (Wild-type sequence corresponding to DEL is SEQ ID NO: 25; Wild-type sequence correspondent of E208Q is SEQ ID NO: 27), indicating that the mutations are somatic.

In Panel A, samples were pre-incubated with either DMSO or JAK inhibitor I (5 µM) for 30 minutes, and then stimulated with either TPO (50 ng/ml) or G-CSF (20 ng/ml) for 15 minutes, prior to assessment of STAT3 and STAT5 activation by phospho-specific flow cytometry. Panel B shows CD34 and CD38 surface staining for the cytokine-responsive pSTAT3+/5+ ("responsive") cells from DEL, in comparison to the nonresponsive cells (includes all cells other than pSTAT3+/5+ cells). For Panels A and B, numbers depicted in each quadrant represent the percentage of total cells present in each quadrant gate. In Panel C, the frequency of CD34+ cytokine-responsive cells was quantified and is displayed as fold-change versus normal donor. In Panel D, PBMCs from DEL were stimulated with G-CSF, and six subsets were sorted by FACS, as defined by the surface markers and phosphorylated STAT proteins shown in the table. Not applicable (n/a) denotes surface markers that were not used to delineate that specific subset. DNA was isolated from each subset, and allele-specific quantitative PCR for the DEL mutation was performed. Allele burden for each subset is displayed. Error bars represent the standard deviation of three replicates.

FIG. 4. Fold-change for JAK2, STAT3, and STAT5 activation in BaF3-MPL cells stimulated with TPO. MFIs for each time point were normalized to unstimulated cells (0 min) for each cell line and represented as fold-change. This data is displayed visually as histograms in FIG. 2B.

Figure 5:
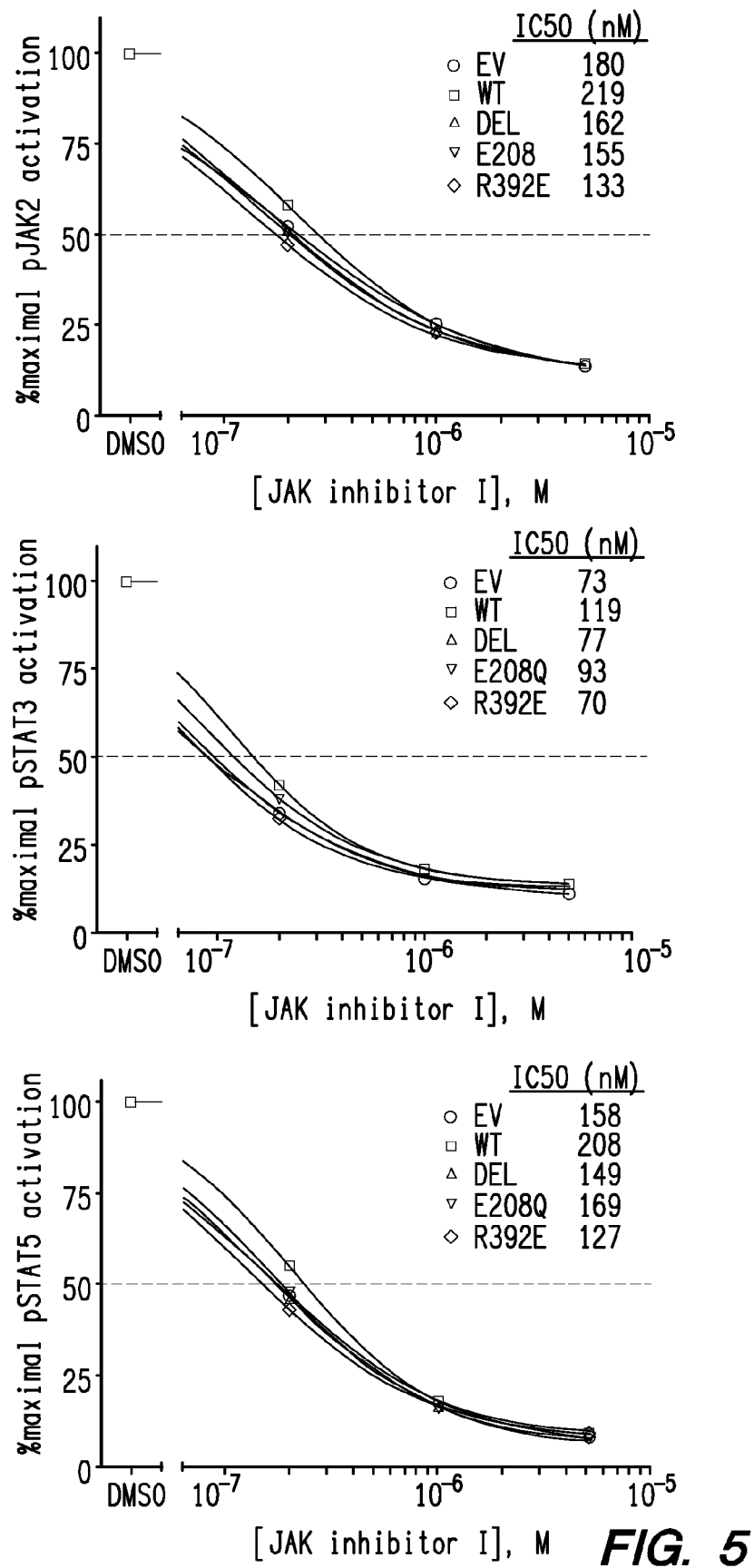

FIG. 5. Activation of JAK2-STAT3/5 in BaF3-MPL cells expressing WT or mutant LNK requires JAK activity. BaF3-MPL cells expressing WT or mutant LNK were pre-incubated with DMSO or JAK inhibitor I at concentrations ranging from 0.2 µM to 5 µM for two hours prior to stimulation with TPO (10 ng/mL). JAK2, STAT3, and STAT5 activation were then measured by phospho-specific flow cytometry. Line graphs represent % maximal activation for each cell line.

Figure 6:
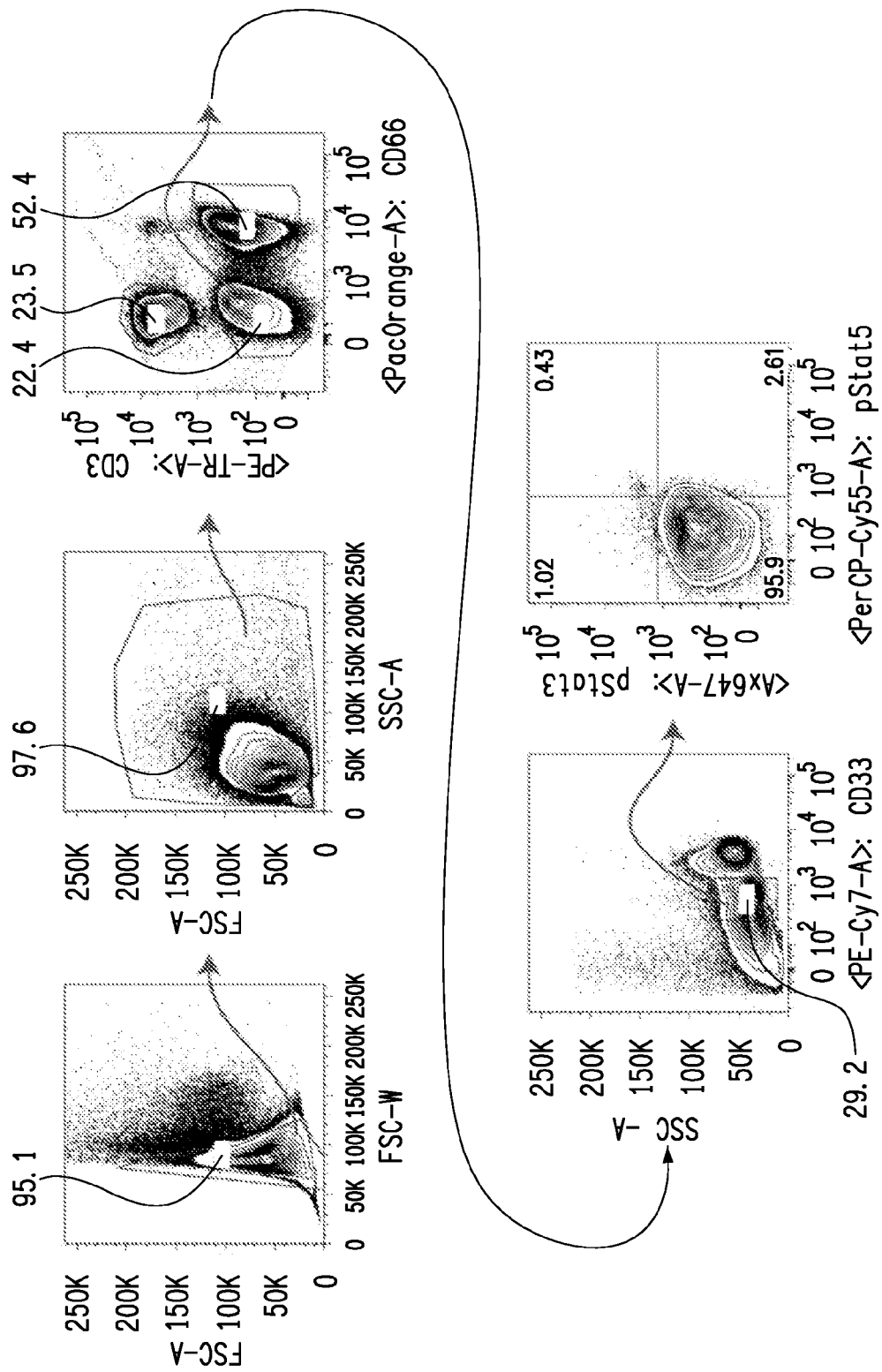

FIG. 6. Upstream gating strategy for FIG. 3A-C. Singlets were gated based on forward and side scatter. CD3 and CD66 were then used to eliminate T-cells and granulocytes, respectively. Initial studies indicated that CD33hi cells were CD14+ (mature monocytes) and did not exhibit STAT3/5 phosphorylation in response to TPO and/or G-CSF. CD33mid cells were CD14– (immature myeloid cells) and were therefore used for analysis of pSTAT3 and pSTAT5.

Figures 7A, 7B, 7C:
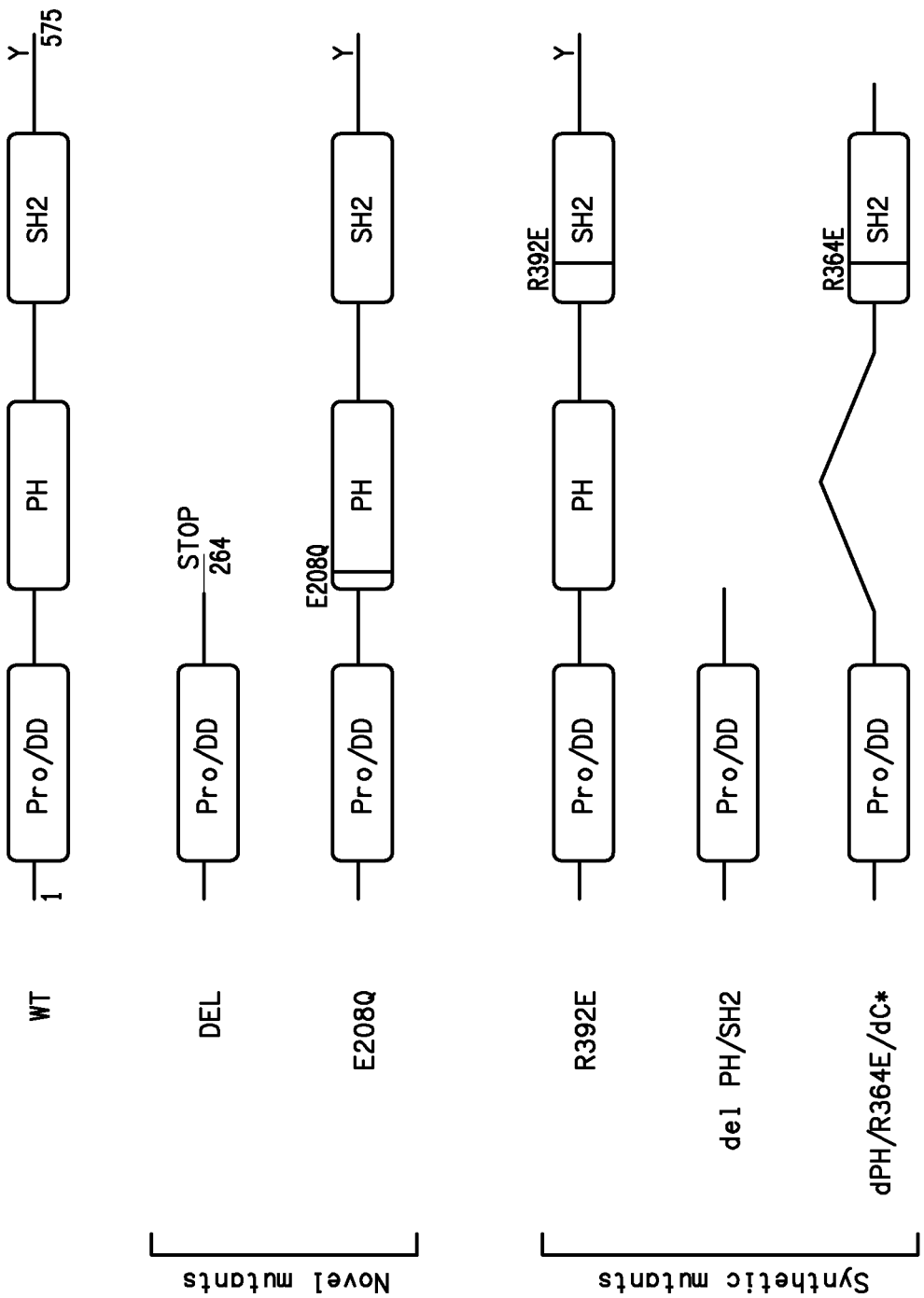

FIG. 7: Domain structure of wild-type and mutant LNK. (A) Wild-type LNK is 575 amino acids and consists of an N-terminal proline rich domain and dimerization domain (Pro/DD), a pleckstrin homology (PH) domain important for targeting to the plasma membrane, an SH2 domain that interacts with MPL and JAK2, and a conserved tyrosine residue (Y) at the C-terminus. (B) The DEL mutant contains a 5 bp deletion and missense mutation, leading to a premature stop codon and a truncated protein of 264 amino acids. The E208Q mutant contains a point mutation resulting in a glutamic acid to glutamine alteration at amino acid 208, located at the beginning of the PH domain. (C) The R392E mutant has been shown to disrupt the SH2 domain and abolish the ability of LNK to inhibit TPO-mediated signaling and proliferation (Gery et al, Blood 2007). The del PH/SH2 mutant loses the ability to localize to the plasma membrane (Gery et al, Blood 2007). The dPH/R364E/dC mutant exerts a dominant-negative effect on wild-type Lnk (Takizawa et al, Blood 2006).

DESCRIPTION OF THE SPECIFIC EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods for Diagnosing or Predicting a Hematolymphoid Neoplasm or Malignancy

Aspects of the present invention include methods of classifying a subject as having or being predisposed to a hematolymphoid neoplasm or malignancy, comprising:

determining the sequence of an LNK gene derived from a sample from the subject, wherein the sample from the subject comprises blood cells; and classifying the subject as having or being predisposed to a hematolymphoid neoplasm or malignancy if the determined LNK sequence has at least one mutation.

In certain embodiments, the LNK mutation is within the pleckstrin homology (PH) and/or SH2 domains. In certain embodiments, the LNK mutation is a deletion of all or a portion of the pleckstrin homology (PH) and/or SH2 domains. In certain embodiments, the LNK mutation results in an increase in cytokine signaling in a cell as compared to wild type LNK. In certain embodiments, the LNK mutation is selected from: E208Q and 603_607delGCGCT; 613C>G.

In certain embodiments, the sample is a blood sample.

In certain embodiments, the hematolymphoid neoplasm or malignancy is a JAK2 V617F-negative myeloproliferative neoplasm (MPN).

In certain embodiments, the classifying step comprises comparing the determined LNK sequence to one or more reference LNK sequence, wherein the one or more reference LNK sequence includes one or both of:

an LNK sequence from a subject known to be predisposed to a hematolymphoid neoplasm or malignancy; and an LNK sequence from a subject known not to be predisposed to a hematolymphoid neoplasm or malignancy.

Any convenient method for determining the sequence of an LNK nucleic acid or protein may be employed, and as such no limitation in this regard is intended. In certain embodiments, the determining step comprises one or more of the following: PCR, nucleic acid hybridization, sequencing analysis, and antibody binding assay.

The methods of the present disclosure are suited for the preparation of a report that provides a result or score resulting from the methods of the present disclosure. A "report," as described herein, is an electronic or tangible document which includes report elements that provide information of interest relating to a diagnosis or risk assessment and its results (e.g., an LNK mutation result and likelihood of having or developing a neoplasm/malignancy). A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) genetic test data and 6) other features.

The present disclosure thus provides for methods of creating reports and the reports resulting therefrom. The report may be presented in electronic format or on paper, and may be provided to the patient or the patient's healthcare provider. In certain embodiments, the method disclosed herein can further include a step of generating or outputting a report of the results of methods detailed herein to a user, e.g., a patient or a healthcare provider. A person or entity who prepares a report ("report generator") may also perform an assessment of the date therein. The report generator may also perform any one or more of the process steps, e.g., sample gathering, sample processing, and data generation. Alternatively, an entity other than the report generator can perform one or more sample gathering, sample processing, and data generation.

In certain embodiments, e.g., where the methods are completely executed on a single computer, the user or client provides for data input and review of data output. A "user" can be a health professional (e.g., a clinician, a laboratory technician, a physician (e.g., an oncologist, surgeon, pathologist), etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, may be subjected to a quality control routine prior to release to the user.

The methods provided by the present disclosure may also be automated in whole or in part.

Drug Screening

Aspects of the subject invention include methods of identifying a candidate therapeutic agent for treating hematolymphoid neoplasm or malignancy in a subject, the method comprising:

contacting a cell comprising a mutant LNK protein with an agent, wherein the mutant LNK protein confers increased cytokine signaling to the cell as compared to wild type LNK; and identifying the agent as a candidate therapeutic agent for treating hematolymphoid neoplasm or malignancy in a subject if the agent reduces cytokine signaling in the cell as compared to a control.

In certain embodiments, the LNK mutation is within the pleckstrin homology (PH) and/or SH2 domains. In certain embodiments, the LNK mutation is a deletion of all or a portion of the pleckstrin homology (PH) and/or SH2 domains. In certain embodiments, the LNK mutation is selected from: E208Q and 603_607delGCGCT; 613C>G. In certain embodiments, the LNK mutant is associated with a hematolymphoid neoplasm or malignancy. In certain embodiments, the hematolymphoid neoplasm or malignancy is a JAK2 V617F-negative myeloproliferative neoplasm (MPN).

In certain embodiments, the contacting step further comprises contacting the cell with a cytokine. In certain embodiments, the cytokine is TPO.

Treatment Methods, Therapeutic Agents and Pharmaceutical Compositions Thereof

Aspects of the subject invention include treating a subject having a hematolymphoid neoplasm or malignancy, comprising administering an effective amount of agent that inhibits LNK mutant-mediated increases in cytokine signaling (e.g., from TPO signaling). In certain embodiments, the agent blocks LNK mutant mediated activation of STAT3 and/or STAT5.

Pharmaceutical formulations of therapeutic agents may be optimized for retention and stabilization at a targeted site. Stabilization techniques include enhancing the size of the polypeptide, by cross-linking, multimerizing, or linking to groups such as polyethylene glycol, polyacrylamide, neutral protein carriers, etc. in order to achieve an increase in molecular weight. Other strategies for increasing retention include the entrapment of the polypeptide in a biodegradable or bioerodible implant. The rate of release of the therapeutically active agent is controlled by the rate of transport through the polymeric matrix, and the biodegradation of the implant. The transport of polypeptide through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. The polypeptide may be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Databases of Expression Profiles of Phenotype Determinative Genes

Also provided are databases of LNK gene sequences and their association with hematolymphoid neoplasms or malignancies. The sequences and corresponding associations may be provided in a variety of media to facilitate their use (e.g., in a user-accessible/readable format). "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

As such, the subject invention further includes a computer program product for determining whether a subject has or is predisposed to having a hematolymphoid neoplasm or malignancy. The computer program product, when loaded onto a computer, is configured to employ an LNK gene or protein sequence from a blood cell containing sample to determine a hematolymphoid neoplasm or malignancy category for the subject. Once determined, the clinical hematolymphoid neoplasm or malignancy category is provided to a user in a user-readable format. In addition, the computer program product may include one or more reference or control LNK sequences which are employed to determine the clinical transplant category of the patient.

Reagents, Systems and Kits

Also provided are reagents, systems and kits thereof for practicing one or more of the above-described methods. The subject reagents, systems and kits thereof may vary greatly. Reagents of interest include reagents specifically designed for use in determining LNK nucleic acid and/or protein sequences. The term system refers to a collection of reagents, however compiled, e.g., by purchasing the collection of reagents from the same or different sources. The term kit refers to a collection of reagents provided, e.g., sold, together.

Reagents specifically tailored for determining a sequence of an LNK gene or protein include a collection of LNK specific primers or probes, at least one of which is designed to selectively detect and/or amplify an LNK mutant gene/cDNA (etc.) (e.g., using hybridization assay, a PCR-based technique, linear amplification, etc.). The systems and kits of the subject invention may include an antibody specific for a mutant amino acid sequence (e.g., for a positive screening assay) or for a sequence known to be deleted in a LNK mutant (e.g., in negative screening assay). The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, primary and secondary antibodies (including labeled antibodies) enzymes, such as reverse transcriptases, DNA polymerases, RNA polymerases, and the like, various buffer mediums, e.g. hybridization and washing buffers, prefabricated probe arrays/substrates, labeled probe purification reagents and components, like spin columns, etc., signal generation and detection reagents, e.g. streptavidin-alkaline phosphatase conjugate, chemifluorescent or chemiluminescent substrate, and the like.

The subject systems and kits may further include reagents for peptide or protein level determination, for example those that find use in ELISA assays, Western blot assays, MS assays (e.g., LC-MS), HPLC assays, flow cytometry assays, and the like.

The subject systems and kits may also include a phenotype determination element, which element is, in many embodiments, reference or control sequences that can be employed, e.g., by a suitable computing means, to determine a hematolymphoid neoplasm or malignancy category for a subject based on an "input" lnk nucleic acid or protein sequence.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Summary

LNK is an adaptor protein that inhibits thrombopoietin (TPO) and JAK2. Here we report novel LNK mutations in two patients with JAK2 V617F-negative myeloproliferative neoplasms. One patient exhibited a 5 base-pair deletion and missense mutation leading to a premature stop codon and loss of the pleckstrin homology (PH) and SH2 domains. A second patient had a missense mutation (E208Q) in the PH domain. BaF3-MPL cells transduced with these LNK mutants displayed dysregulated TPO-dependent growth and signaling. Cytokine-responsive CD34+ cells were abnormally abundant in both patients. Thus, loss of LNK negative feedback regulation drives aberrant JAK-STAT signaling and constitutes a novel mechanism of MPN pathogenesis.

Introduction

Aberrant signaling due to activating mutations in tyrosine kinases is a hallmark of chronic myeloproliferative neoplasms (MPNs). The V617F mutation in exon 14 of JAK2 has been described in >95% of patients with polycythemia vera (PV), and approximately 50% of patients with essential thrombocythemia (ET) and primary myelofibrosis (PMF) (refs 1-4). Gain-of-function mutations in exon 12 of the JAK2 gene have been found in the small minority of PV patients without the V617F mutation (ref. 5), and activating mutations in the thrombopoietin (TPO) receptor MPL (W515K/L) have been identified in approximately 5% of patients with JAK2 V617Fnegative PMF and ET. (refs. 6, 7) Thus, approximately 40-50% of ET and PMF patients lack a defined genetic abnormality. Even in the absence of mutations in JAK2 or MPL, activation of JAK-STAT signaling can be demonstrated in some MPN patients (refs. 8-10), suggesting that alterations of other regulatory elements in this pathway may contribute to MPN pathogenesis.

One regulator of JAK-STAT signaling is LNK (SH2B3), a member of a family of adaptor proteins that share several structural motifs, including a proline-rich N-terminal dimerization domain, a pleckstrin homology (PH) domain, an SH2 domain, and a conserved tyrosine residue near the C-terminus (ref. 11) (FIG. 1A). LNK binds constitutively to MPL via its SH2 domain and co-localizes to the plasma membrane via its PH domain. (refs. 12, 13) Upon cytokine stimulation with TPO, LNK binds strongly to JAK2 and dampens or terminates downstream STAT activation. (ref. 12) LNK-/- mice exhibit features consistent with an MPN phenotype, including an expanded hematopoietic stem cell (HSC) compartment, megakaryocytic hyperplasia, splenomegaly, leukocytosis, and thrombocytosis. (refs. 14-16) This phenotype is TPO-dependent, as LNK-/- mice crossed with TPO-/- mice do not display these features. (ref 17) In addition, LNK-/- HSCs display potentiated activation of JAK2 in response to TPO stimulation. (ref. 12) These studies provide compelling evidence that LNK plays a central role in the regulation of hematopoiesis, and that abrogation of LNK activity may be an important pathogenetic feature of MPNs. We therefore sequenced LNK in a cohort of JAK2 V617F-negative MPNs, and now report the identification of novel LNK mutations that lead to dysregulated JAK-STAT signaling and growth.

Results

Identification of Somatic LNK Mutations in JAK2 V617F-negative MPNs

Direct sequencing of the region of LNK encompassing the PH and SH2 domains (partial exon 2 through exon 7) (FIG. 1A) was performed on samples from 33 patients with JAK2 V617F-negative MPNs (as defined by the World Health Organization) (Table 1), resulting in the identification of two novel mutations in exon 2 of LNK. As shown in FIG. 1B, a 5 bp deletion and missense mutation (NM_005475.2:c. [603_607delGCGCT; 613C>G], henceforth referred to as DEL), leading to a premature stop codon was identified in patient 01 with PMF. This mutation results in the absence of both the PH and SH2 domains (FIGS. 1C and D).

In patient 02 with ET (case history in FIG. 4), a missense mutation (NM_005475.2:c.622G>C) leading to a glutamic acid to glutamine substitution (E208Q) localizing to the PH domain was identified. Both cases were negative for MPL W515 mutations (data not shown). Sequencing of germline DNA from these patients' cultured skin fibroblasts revealed wild-type LNK sequence (FIG. 1E), confirming that these mutations were somatic. Neither of these mutations has been reported in publicly available SNP databases. Overall, the frequency of LNK mutations identified in our cohort of JAK2 V617F-negative MPN patients was 2/33 (6%).

Figure 2A:
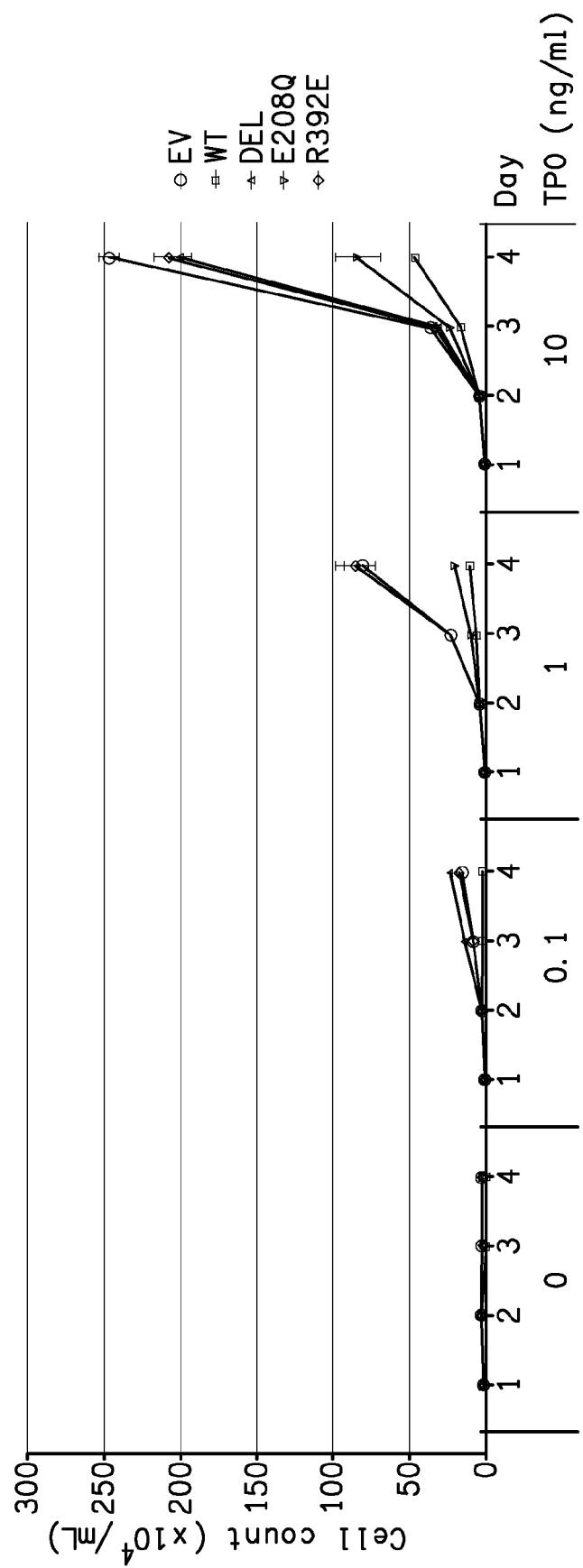
FIG. 2. LNK mutations cause dysregulated TPO-dependent growth and JAK2-STAT3/5 activation. BaF3-MPL cells were transduced with empty vector (EV), WT LNK (WT), or mutant LNK (DEL, E208Q, R392E). Panel A shows growth of BaF3-MPL over four days in concentrations of TPO ranging from 0 to 10 ng/ml. Viable cells were counted daily by staining with propidium iodide (PI) and quantitated with Tru-Count beads on a LSRII flow cytometer. Error bars represent the standard deviation of two replicates per sample. In Panel B, BaF3-MPL cells were stimulated with TPO (1 ng/ml) for the durations indicated, followed by measurement of JAK2, STAT3 and STAT5 activation via phospho-specific flow cytometry. Histograms for phosphorylated forms of JAK2 (pJAK2), STAT3 (pSTAT3), and STAT5 (pSTAT5) are displayed, with internal shading representing fold-change in median fluorescence intensities (MFI) compared to unstimulated cells (unstim) for each cell line. Vertical lines denote the MFI of EV unstimulated cells for comparison. In Panel C, BaF3-MPL cells were cultured in the presence of DMSO control or concentrations of JAK inhibitor I ranging from 0.2 µM to 5 µM. Cumulative growth at four days (normalized to maximal growth for each cell line) is shown. Error bars represent the standard deviation of two replicates per sample.

LNK Mutations Cause Dysregulated TPO-Dependent Growth and STAT3/5 Activation To investigate the functional effects of LNK mutations in MPN pathogenesis, wild-type (WT) or mutant LNK forms were retrovirally expressed in the TPO-dependent BaF3-MPL cell line. BaF3-MPL cells exhibited TPO dose-dependent growth that was inhibited by expression of WT LNK (FIG. 2A). Consistent with prior studies (ref. 13), a synthetic point mutation disrupting the SH2 domain (R392E) abolished LNK-mediated inhibition of TPO-dependent growth. Similarly, the DEL mutant lacked the ability to inhibit TPO-mediated growth, consistent with a loss of LNK negative feedback function. In contrast, the E208Q mutant retained partial inhibitory activity, suggesting that LNK mutations may confer a spectrum of phenotypes. This differential effect was further underscored below during analysis of JAK-STAT signaling in primary samples from MPN patients bearing these mutations.

Figure 2B:
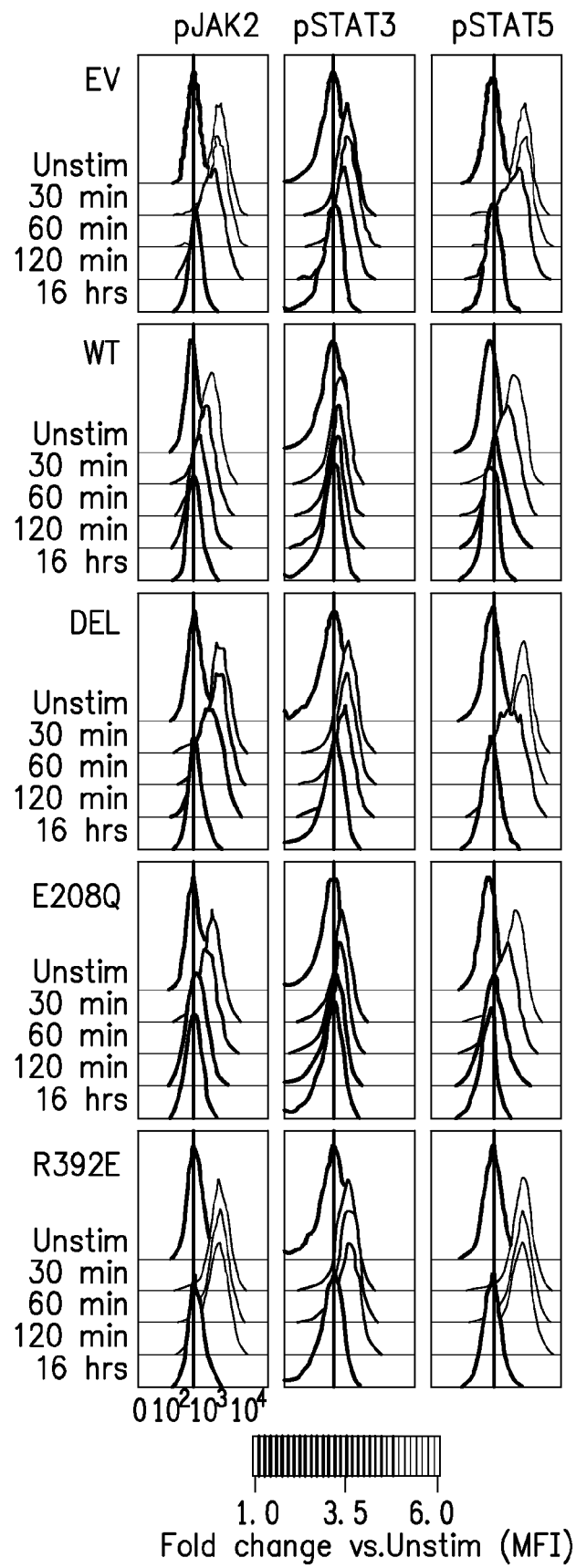

LNK inhibits TPO-mediated proliferation by binding to MPL and JAK2 and blocking downstream STAT3/5 activation. (refs. 12, 13) Therefore, we investigated the effects of LNK mutations on TPOmediated activation of the JAK2-STAT3/5 pathway. BaF3-MPL cells expressing WT and mutant LNK were stimulated with TPO, and JAK2, STAT3, and STAT5 phosphorylation (activation) was measured via phospho-specific flow cytometry (FIG. 2B and FIG. 4). In BaF3-MPL cells transduced with empty vector (EV), stimulation with TPO (1 ng/ml) resulted in robust activation of the JAK2-STAT3/5 pathway that peaked at approximately 30 minutes and was sustained until 60 minutes. In contrast, cells expressing WT LNK exhibited reduced activation of JAK2-STAT3/5, which peaked transiently at 30 minutes and declined immediately. BaF3-MPL cells expressing the SH2 domain mutant R392E lost the inhibitory capacity of LNK and achieved maximal and sustained activation of JAK2-STAT3/5 from 30 to 120 minutes, twice as long as EV. Cells expressing the DEL mutant performed similarly to EV, exhibiting sustained JAK2-STAT3/5 activation at 30 to 60 minutes. The E208Q mutant retained near-complete inhibitory capacity in this system, suggesting that it may confer a subtle loss of function, consistent with the partial inhibition seen in the growth assays. These findings are consistent with previous studies showing that LNK plays an important role in terminating JAK-STAT signaling following cytokine stimulation (ref. 12), such that loss of function mutations may permit the unabated JAK-STAT activation and increased cellular proliferation commonly observed in MPNs.

Figure 2C:
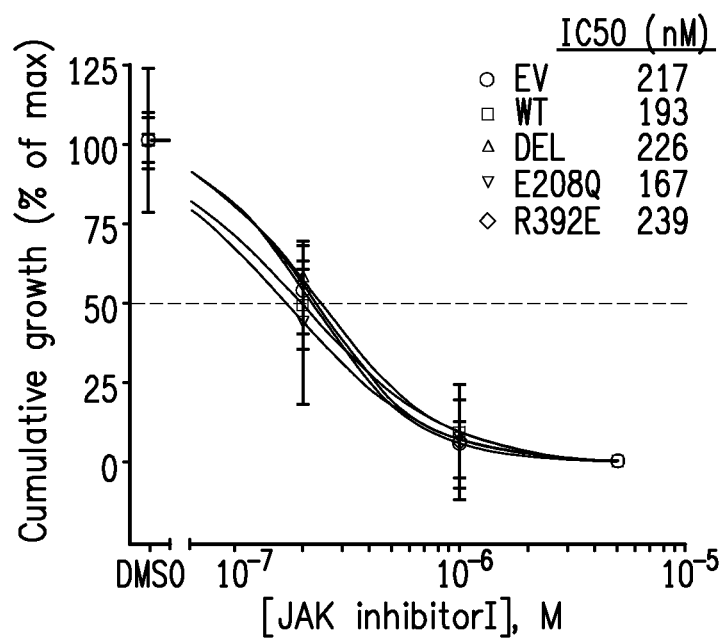

To further assess the role of JAK2 in LNK-mediated inhibition of TPO-dependent STAT3/5 activation and proliferation, BaF3-MPL cells were cultured in the presence of a pan-JAK inhibitor (JAK inhibitor I). BaF3-MPL cells expressing WT or mutant LNK remained susceptible to JAK inhibition, with a similar 1050 for each cell line (FIG. 2C). Similarly, JAK2-STAT3/5 activation was effectively inhibited by JAK inhibitor I in all cell lines (FIG. 5). These findings confirm that in the presence of WT or mutant LNK, TPO-mediated growth and STAT activation can be abrogated by JAK inhibition.

Figure 3A:
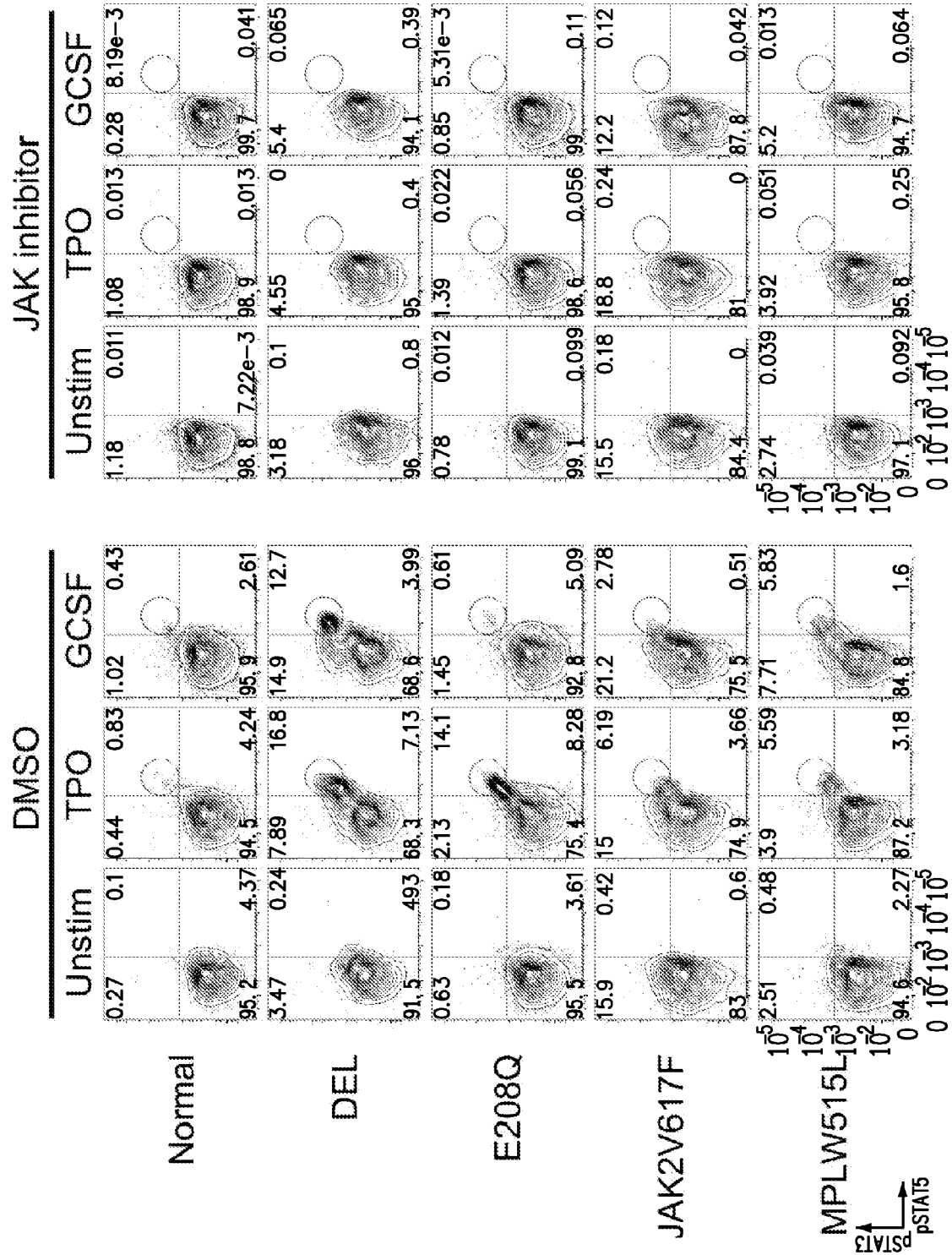
FIG. 3. Identification of a cytokine-responsive pSTAT3+/pSTAT5+ population in CD34+ early progenitors from patients with LNK mutations. Peripheral blood samples from patients with the LNK DEL and E208Q mutations, as well as PMF patients with the JAK2 V617F and MPL W515L mutations, were compared with normal donor. CD3-/CD66-/CD33mid immature myeloid cells are shown in Panels A-C.

LNK Mutations are Associated with Aberrant JAK-STAT Activation in the CD34+ Early Progenitor Compartment We examined JAK-STAT signaling in circulating immature myeloid cells (FIG. 6) from normal donor as well as MPN patients bearing LNK, JAK2 V617F, or MPL W515L mutations. As shown in FIG. 3A (left), stimulation with TPO or G-CSF revealed a unique phosphorylated STAT3/5 (pSTAT3+/5+) subpopulation that was markedly increased in DEL compared with normal donor samples. A similar cytokine-responsive pSTAT3+/5+ subpopulation was observed with JAK2 V617F-positive and MPL W515L-positive PMF samples, suggesting that this may be a shared phenotype among PMF patients. Interestingly, cells from the patient bearing the E208Q mutation exhibited heightened STAT3/5 phosphorylation in response to TPO, but not GCSF, suggesting that a partial loss of LNK function may generate differential STAT activation profiles in response to specific cytokines. STAT3/5 activation was also measured in the presence of JAK inhibitor I (FIG. 3A, right). In each case, the pSTAT3+/5+ subpopulation was completely eradicated by JAK inhibition, confirming that STAT3/5 activation was dependent on JAK activity.

Figure 3B:
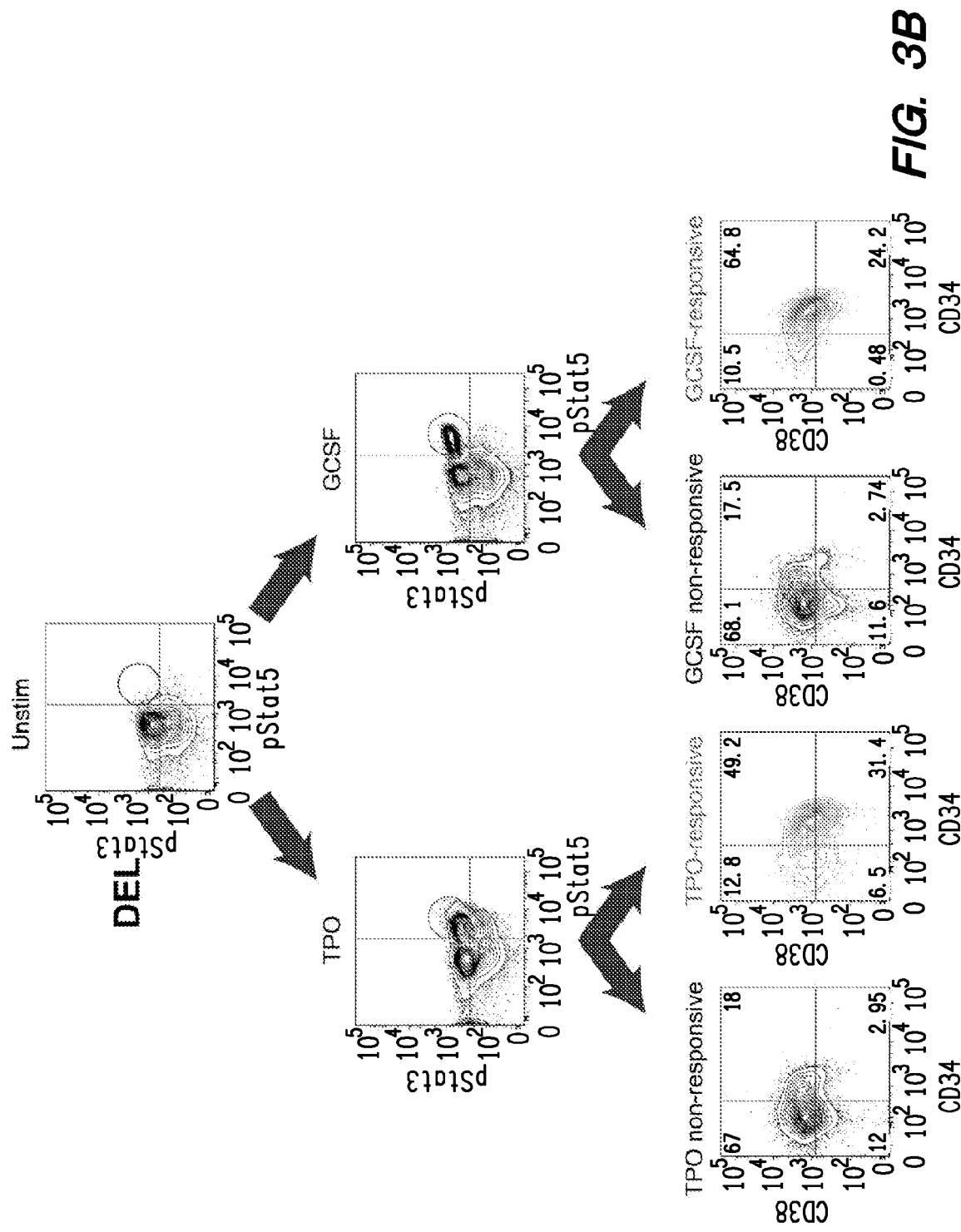
Figure 3C:
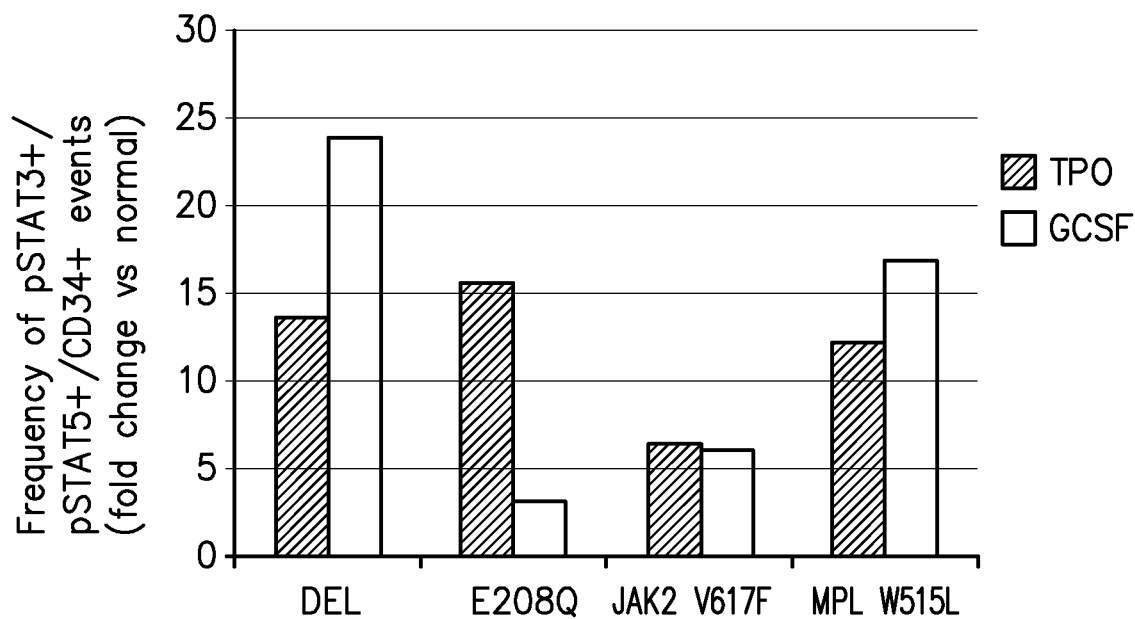

In order to further characterize the cytokine-responsive pSTAT3+/5+ ("responsive") population, we performed extended surface marker analysis on this subset. As shown in FIG. 3B, the responsive cells from DEL were predominantly CD34+ (81% of TPO-responsive and 89% of GCSF-responsive), suggesting that the responsive cells primarily consisted of early progenitors and/or HSCs. In addition, when comparing cytokine-responsive versus non-responsive cell populations, CD34+ expression was markedly increased among the responsive cells, indicating that cytokine responsiveness may be a distinctive feature of the early progenitor compartment. We calculated the overall frequency of CD34+ responsive cells (FIG. 3C), and found that this subpopulation was markedly increased in DEL compared with normal donor. Similar results were found for JAK2 V617F-positive and MPL W515L-positive PMF samples. In E208Q, TPOresponsive, but not G-CSF-responsive, CD34+ cells were increased. These findings suggest that TPO and/or G-CSF-mediated activation of STAT3/5 in the CD34+ early progenitor compartment is a recurring feature in MPNs, but that there may be a spectrum of phenotypes.

Figure 3D:
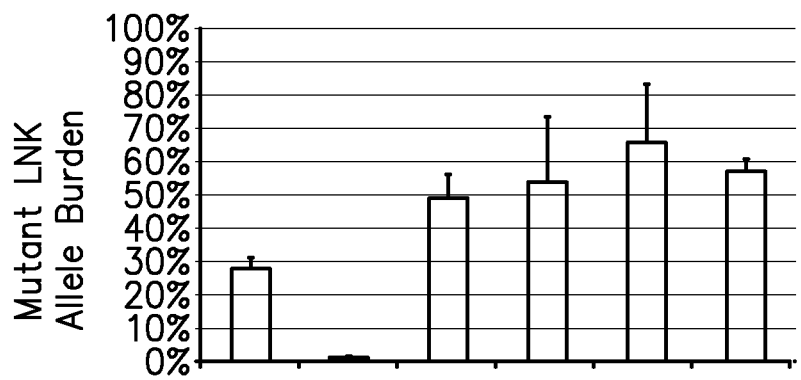

Given the abnormal abundance of cytokine-responsive CD34+ cells in DEL, we investigated whether the LNK mutation was present in these cells. As shown in FIG. 3D, allele-specific quantitative PCR confirmed the presence of the DEL mutation in the cytokine-responsive cells. In addition, the absence of the DEL mutation in T cells suggests that the mutation was restricted to the myeloid lineage. Finally, mutant allele burden was ~50% in all myeloid cells examined, consistent with a heterozygous mutation. These findings suggest that LNK mutations arise in the CD34+ early progenitor compartment and represent an early genetic event in MPN pathogenesis.

Discussion

Our identification of mutations in the LNK gene in a subset of MPN patients, the first linked to any human disease, demonstrates that disruption of an inhibitory adaptor protein can phenocopy a disease typically driven by activating mutations in tyrosine kinases (i.e. JAK2, MPL). We detected LNK mutations in 2/33 (6%) JAK2 V617F-negative MPN patients. This frequency is similar to the occurrence of MPL W515 mutations in ET and PMF, but screening of a larger cohort will be necessary to determine the true frequency of LNK mutations and their relevance to MPN clinicopathologic features and prognosis. Since prior in vitro studies have demonstrated that LNK can inhibit the activity of both MPL W515L and JAK2 V617F (refs. 13, 18), it is conceivable that loss of LNK function may occur as a cooperative event in the pathogenesis of these MPNs as well.

Both LNK mutations described here affect the PH domain, and mutations in the PH domains of other proteins (e.g. AKT1) have been reported in solid tumors (refs. 19, 20), suggesting that this may be an increasingly recognized mechanism of tumorigenesis. Since the PH domain of LNK is important for plasma membrane localization, the DEL and E208Q mutations could result in mislocalization of LNK and altered ability to bind to MPL and JAK2 and inhibit downstream STAT activation. Indeed, a synthetic LNK mutant in which the PH domain was deleted could no longer localize to the plasma membrane. (ref. 13) The DEL mutant also lacks the SH2 domain, which could explain its more complete loss of function. This is supported by prior studies in which a synthetic point mutation affecting the PH domain resulted in partial loss of LNK function (similar to E208Q), while mutations affecting the SH2 domain eliminated binding to MPL and JAK2 and resulted in a more severe phenotype. (refs. 12, 13, 16, 21)

Our allele-specific quantitative PCR results suggest that the DEL mutation is heterozygous, invoking the notion that loss of one functional LNK allele (i.e. haploinsufficiency) may be sufficient to initiate MPN pathogenesis in these cases. In murine studies, the absence of LNK function (LNK-/-) led to an MPN phenotype, while heterozygosity (LNK+/-) conferred an intermediate phenotype, consistent with a haploinsufficiency model (ref. 15). Alternatively, as the Nterminal proline-rich dimerization domain is retained with both the DEL and E208Q mutations, mislocalization of mutant LNK could lead to sequestering of WT LNK, thereby leading to functional loss of both LNK alleles (i.e. trans-dominance). This hypothesis is supported by a previous study in which a synthetic mutant disrupting both the PH and SH2 domains exerted a dominant negative effect. (ref. 22)

LNK is a critical component of a negative feedback loop, such that cytokine stimulation with TPO induces LNK to bind strongly to JAK2 and dampen or terminate downstream STAT activation (ref. 12). This negative regulation is integral to normal hematopoiesis and modulation of HSC growth and development. Our findings indicate that mutation of LNK disrupts this feedback axis, thereby permitting potentiated and sustained STAT3/5 activation in response to cytokine stimulation and causing increased proliferation, as demonstrated by the BaF3-MPL growth assays. These effects were manifested physiologically as an overabundance of cytokine-responsive CD34+ early progenitors in MPN patients bearing LNK mutations. Furthermore, the presence of the DEL mutation in the CD34+ compartment suggests that disruption of LNK confers a growth advantage to these cells and may be an early genetic event in MPN pathogenesis, similar to previous findings with JAK2 V617F in PV. (ref. 23) The pSTAT3+/5+ response in primary samples from patients carrying LNK mutations was also found in PMF patients bearing JAK2 V617F or MPL W515L mutations. Clearly, JAK-STAT activation is a principal characteristic of MPN biology; in the absence of JAK2 or MPL mutations, LNK mutations may drive this aberrant response. Furthermore, the abnormal pSTAT3+/5+ response is reminiscent of subpopulations observed in acute myelogenous leukemia (ref. 24), suggesting that this signaling phenotype is a recurring feature found in a spectrum of myeloid neoplasms. Since TPO-mediated signaling and growth of cell lines and primary samples bearing LNK mutations were effectively inhibited by a JAK inhibitor, treatment with JAK2 inhibitors may be feasible for patients with LNK mutations. Indeed, in early phase trials with JAK2 inhibitors, responses have been observed in both JAK2 V617F-positive and -negative MPN patients (ref. 25), and it will therefore be of interest to screen these latter individuals for LNK mutations.

Methods

Clinical Samples

All clinical samples were obtained with informed consent and with approval by the Institutional Review Board of Stanford University School of Medicine. Peripheral blood samples were obtained in sodium heparin and stimulated immediately with cytokines, or following isolation of peripheral blood mononuclear cells (PBMCs) with Ficoll density gradient separation according to standard procedures. (refs. 24, 26) Skin fibroblasts were isolated by mechanical disaggregation of skin punch biopsies and established in short-term monolayer culture using standard methods.

Sequencing

Genomic DNA (gDNA) was extracted from peripheral blood samples or cultured skin fibroblasts using either the QIAamp DNA Blood Mini or Gentra Purgene Blood Kit (Qiagen, Valencia, Calif.) according to the manufacturer's instructions. Quality and quantity of gDNA was assessed using a Nanodrop Spectrophotometer (Thermo Scientific, Wilmington, Del.). PCR and sequencing primers for LNK exons 2 through 7, covering the PH and SH2 domains, were designed as follows:

```
                                              (SEQ ID NO: 1)
LNK_PART_EX2_F:  CGGAGAGGCTGCTGAGAC (SEQ ID NO: 2)
LNK_PART_EX2_R:  TTGCACTCGGCCTAAAAGTT (SEQ ID NO: 3)
LNK_PART_EX2_F nest:  AAGAAGTTCCTGCCCTGGAG (SEQ ID NO: 4)
LNK_PART_EX2_R nest:  CTGGAAAGCCATCACACCTC (SEQ ID NO: 5)
LNK EX 3-5_F:  AACTCAGGCCTGGCTGG (SEQ ID NO: 6)
LNK EX 3-5_R:  GGGCTACCTTATGTCCTGGG (SEQ ID NO: 7)
LNK Ex 3-5_F INTSEQ:  GGTGGGAGACGAGCAG (SEQ ID NO: 8)
LNK Ex 3-5_R INTSEQ:  CTGTGCACTCCGAGAGC (SEQ ID NO: 9)
LNK_Ex6-7_F:  GTACGCTGGAACCCAGACTC
```

```
                                           (SEQ ID NO: 10)
LNK_Ex6-7_R:   GTCTGCAGCAAGCCTCTACC (SEQ ID NO: 11)
LNK_Ex6-7_Nest_F:  ACTCAGCCCAGGACATAAGG (SEQ ID NO: 12)
LNK_Ex6-7_Nest_R:  GCCTCTACCCTCTACCCAGTG (SEQ ID NO: 13)
LNK_EX6_NEST_SEQF:  GCTCATGGAGTGTTCCTGGT (SEQ ID NO: 14)
LNK_EX6_NEST_SEQR:  AGGTGCTGTGGGAGGAGAG
```

Touchdown PCR was performed according to standard protocols, followed by agarose gel electrophoresis to check for adequate amplification prior to sequence analysis. Bi-directional sequencing was performed using BigDye v3.1 (Applied Biosystems, Foster City, Calif.) and the Applied Biosystems 3100 or 3730×1 DNA Analyzer, according to the manufacturer's protocols.

Cell Culture

BaF3-MPL cells were kindly provided by J. Tyner/B. Druker (Oregon Health and Sciences University, Portland, Oreg.) and were maintained in RPMI medium containing 10% FBS and IL-3 (1 ng/mL) (Peprotech, Rocky Hill, N.J.). For the growth assays, BaF3-MPL cells were washed twice in cytokine-free media and re-plated in RPMI with 10% FBS and TPO (0-10 ng/mL) (Peprotech, Rocky Hill, N.J.). For the JAK inhibitor growth assays, BaF3-MPL cells were grown with TPO (10 ng/mL) in the presence of DMSO control or JAK inhibitor I (EMD/Calbiochem, San Diego, Calif.) at various concentrations. Viable cells were counted daily by staining with propidium iodide (PI) and quantitated with Tru-Count beads (BD Biosciences, San Jose, Calif.) on a LSRII flow cytometer. Phoenix-Eco retroviral packaging cells were maintained in DMEM media containing 10% FBS.

Expression Vectors

Wild-type LNK and DEL sequences were synthesized by DNA 2.0 (Menlo Park, Calif.) in a Gateway-compatible donor vector. The pSRα retroviral expression vector was kindly provided by J. Tyner/B. Druker and converted into a Gateway-compatible destination vector (pSRα-GW) using the Gateway Vector Conversion System (Invitrogen, Carlsbad, Calif.) according to the manufacturer's instructions. WT and DEL sequences were transferred to pSRα-GW using LR clonase (Invitrogen, Carlsbad, Calif.). The E208Q and R392E mutants were generated from WT LNK using the QuikChange Lightning Kit (Stratagene, La Jolla, Calif.) and were verified by direct sequencing.

Retroviral Transduction

Retroviral expression vectors were transfected into Phoenix-Eco cells using Lipofectamine 2000 (Invitrogen, Carlsbad, Calif.). Retroviral supernatants were collected two days following transfection, added to BaF3-MPL cells with polybrene (4 mg/ml) on retronectin-coated plates, and centrifuged at 1500×g for 90 minutes. Two days after transduction, cells were selected in G418 (750 ng/ml) for at least a week, until transduced cells were growing stably.

Cytokine Stimulation and Phospho-Specific Flow Cytometry

BaF3-MPL cells were starved overnight in cytokine-free media and stimulated with TPO (1 or 10 ng/mL) for time points ranging from 15 minutes to 16 hours at 37° C. Peripheral blood samples were stimulated with either TPO (50 ng/ml) or G-CSF (20 ng/ml)(Peprotech, Rocky Hill, N.J.) for 15 minutes at 37° C. PBMCs were rested in RPMI with 10% FBS for one hour at 37° C. prior to cytokine stimulation. For the JAK inhibitor experiments, PBMCs were incubated with 5 μM JAK inhibitor I (EMD/Calbiochem, San Diego, Calif.) for the final 30 minutes prior to cytokine stimulation. Following cytokine stimulation, cells were fixed in paraformaldehyde (Electron Microscopy Sciences, Hatfield, Pa.). For peripheral blood samples, red blood cells were lysed in hypotonic conditions. Fixed cells were then permeabilized in ice-cold methanol and stained for cell surface markers and/or intracellular phospho-specific epitopes according to standard procedures. (refs. 24, 26) The following antibodies were used (unless otherwise noted, all antibodies were obtained from BD Biosciences, San Jose, Calif.): pSTAT3 (pY705, clone 4/P), pSTAT5 (pY694, clone 47), pJAK2 (pY1007/1008, Cell Signaling Technology, Danvers, Mass.), CD34 (clone 8G12), CD38 (clone HIT2, Invitrogen, Carlsbad, Calif.), CD14 (clone M5E2), CD66 (clone B1.1), CD33 (clone P67.6), CD3 (clone UCHT1, Beckman Coulter, Brea, Calif.). Cells were measured on a BD LSRII flow cytometer. For sorting experiments, cells were sorted directly into PBS using a BD FAC-SAria II cell sorter. Flow cytometry data was obtained with FACSDiva software and analyzed using FlowJo (Tree Star, Ashland, Oreg.) or Cytobank according to standard procedures. (refs. 24, 26)

Allele-Specific Quantitative PCR

DNA from sorted cells was extracted using RecoverALL (Ambion, Austin, Tex.) according to the manufacturer's instructions. Amplifications were performed on a Rotor-Gene 3000 (Corbett/Qiagen, Valencia, Calif.) using Power SYBR Green PCR Master Mix (Applied Biosystems) with three replicates in the presence of 5% DMSO. Primers hybridizing to both alleles of LNK without discrimination [(SEQ ID NO: 15) GCTGAAGGAGGCGGTGCT and (SEQ ID NO: 16) GCTGTCCATGGAGGCCTCGT)] and primers specific for the mutant (DEL) allele [(SEQ ID NO: 17) GGAGGCGGT-GCTATAGCGT and (SEQ ID NO: 16) GCTGTCCATG-GAGGCCTCGT)] were used to amplify either total or mutant LNK. Separate standard curves were constructed using serial dilutions of WT or mutant LNK DNA plasmids. The relative presence of the mutant LNK allele was estimated as the ratio of absolute concentration of mutant versus total LNK within the analyzed cell subsets.

TABLE 1

| Patient Diagnoses | |
| --- | --- |
| Diagnosis | # of Patients |
| ET | 14 |
| PMF | 18 |
| MDS/MPN with fibrosis[†] | 1 |

ET: essential thrombocythemia;
PMF: primary myelofibrosis;
MDS/MPN: myelodyspastic syndrome/myeloproliferative neoplasm
[†]Peripheral blood showed leukopenia with dysplastic neutrophils and thrombocytosis; the bone marrow was hypercellular with megakaryocytic clustering with myeloid hyperplasia and severe (4+) fibrosis Clinical Case Reports of the Two Patients with LNK Mutations Patient 01 is a 75 year-old man who presented in 2007 with fatigue. Physical examination was remarkable for splenomegaly greater than 20 centimeters below the costal margin. The white blood cell count was 12,100/mm$^3$, hemoglobin 6.3 g/dL, and platelet count 323,000/mm$^3$. The peripheral blood smear exhibited leukoerythroblastosis including tear drop and nucleated red blood cell forms, and immature myeloid cells. A bone marrow aspirate was aspiculate and cytogenetic analysis was not performed. The marrow core biopsy revealed diffuse and marked fibrosis with megakaryocytic hyperplasia and clustering. Flow cytometry revealed 6% blasts in the peripheral blood, and 8% in the marrow. JAK2 V617F mutation analysis was negative. A diagnosis of primary myelofibrosis was rendered. The patient has been red blood cell transfusion-dependent and unresponsive to several therapies including prednisone, danazol, erythropoietin, and hydroxyurea. He is currently being considered for a JAK2 inhibitor clinical trial.

Patient 02 is a 59 year-old man who presented in 2002 with a platelet count of 1.2 million/mm$^3$ and otherwise normal blood counts. Organomegaly was not present on examination. Reactive causes of thrombocytosis were excluded. The peripheral blood smear demonstrated giant platelet forms without other significant morphologic abnormalities and a bone marrow biopsy was normocellular with increased megakaryocytes, consistent with essential thrombocythemia. Cytogenetics were normal and JAK2 V617F mutation analysis was negative. He has been treated with aspirin and intermittent use of cytoreductive agents including anagrelide and hydroxyurea, without any thrombohemorrhagic complications.

Further Studies

Examination of Intracellular Localization of LNK Mutants:

Previous studies have shown that LNK localizes to the plasma membrane via the PH domain, where it directly interacts with MPL and JAK2 (Bersenev et al., J. Clin. Invest 2008, 118:2832-2844; and Gery et al., Blood 2007, 110:3360-3364). The LNK SH2 mutant R392E and a deletion mutant lacking the SH2 domain both retain the capacity to localize to the plasma membrane. However a deletion mutant lacking both the SH2 domain and the PH domain (del PH/SH2) loses this capacity (Gery et al., Blood 2007, 110:3360-3364). This mutant, which retains the N-terminus of LNK (including a dimerization domain), followed by a premature stop codon just before the PH domain, is strikingly similar to the LNK DEL mutant that we have identified (FIG. 7). Therefore, we predict that the LNK DEL mutant will also no longer localize to the plasma membrane. In order to test this hypothesis, we will perform immunofluorescence experiments in which cells expressing wild-type LNK and the LNK DEL and E208Q mutants will be stained with LNK-specific antibodies and examined with confocal microscopy. Commercially available antibodies specific for LNK are available, but we plan to introduce an epitope tag (e.g. HA-tag) at the N-Terminus of LNK in order to facilitate these experiments.

Assessment of LNK Mutants as Potential Dominant Negatives:

The newly described LNK DEL and E208Q mutants may lack some or all of wild-type LNK functions. In addition, when expressed in the presence of the wild-type LNK protein (as in the heterozygous state as described for the patients carrying these mutations), they may act as dominant negatives. This is particularly true for the LNK DEL mutant, which likely loses the ability to localize to the plasma membrane due to the absence of the PH domain. However, as this mutant retains the dimerization domain, we speculate that it may dimerize with wild-type LNK and cause mis-localization of the wild-type protein as well. This notion is further supported by previous studies in which a similarly structured mutant (containing a deletion of the PH domain and a point mutation disrupting the SH2 domain) (FIG. 7) has been shown to have the capacity to exert a dominant negative effect (Takizawa et al., Blood 2006, 107:2968-2975).

REFERENCES

1. Baxter E J, Scott L M, Campbell P J, et al. Acquired mutation of the tyrosine kinase JAK2 in human myeloproliferative disorders. Lancet 2005; 365:1054-61.
2. James C, Ugo V, Le Couedic J P, et al. A unique clonal JAK2 mutation leading to constitutive signalling causes polycythaemia vera. Nature 2005; 434:1144-8.
3. Kralovics R, Passamonti F, Buser A S, et al. A gain-of-function mutation of JAK2 in myeloproliferative disorders. N Engl J Med 2005; 352:1779-90.
4. Levine R, Wadleigh M, Cools J, et al. Activating mutation in the tyrosine kinase JAK2 in polycythemia vera, essential thrombocythemia, and myeloid metaplasia with myelofibrosis. Cancer Cell 2005; 7:387-97.
5. Scott L M, Tong W, Levine R, et al. JAK2 exon 12 mutations in polycythemia vera and idiopathic erythrocytosis. N Engl J Med 2007; 356:459-68.
6. Pikman Y, Lee B H, Mercher T, et al. MPLW515L is a novel somatic activating mutation in myelofibrosis with myeloid metaplasia. PLoS Med 2006; 3:e270.
7. Pardanani A, Levine R, Lasho T, et al. MPL515 mutations in myeloproliferative and other myeloid disorders: a study of 1182 patients. Blood 2006; 108:3472-6.
8. Teofili L, Martini M, Cenci T, et al. Different STAT-3 and STAT-5 phosphorylation discriminates among Ph-negative chronic myeloproliferative diseases and is independent of the V617F JAK-2 mutation. Blood 2007; 110:354-9.
9. Heller P, Lev P, Salim J, et al. JAK2V617F mutation in platelets from essential thrombocythemia patients: correlation with clinical features and analysis of STAT5 phosphorylation status. Eur J Haematol 2006; 77:210-6.
10. Mesa R, Tefferi A, Lasho T, et al. Janus kinase 2 (V617F) mutation status, signal transducer and activator of transcription-3 phosphorylation and impaired neutrophil apoptosis in myelofibrosis with myeloid metaplasia. Leukemia 2006; 20:1800-8.
11. Rudd C E. Lnk adaptor: novel negative regulator of B cell lymphopoiesis. Sci STKE 2001; 2001:PE1.
12. Bersenev A, Wu C, Balcerek J, Tong W. Lnk controls mouse hematopoietic stem cell selfrenewal and quiescence through direct interactions with JAK2. J Clin Invest 2008.
13. Gery S, Gueller S, Chumakova K, Kawamata N, Liu L, Koeffler HP. Adaptor protein Lnk negatively regulates the mutant MPL, MPLW515L associated with myeloproliferative disorders. Blood 2007; 110:3360-4.
14. Takaki S, Morita H, Tezuka Y, Takatsu K. Enhanced hematopoiesis by hematopoietic progenitor cells lacking intracellular adaptor protein, Lnk. J Exp Med 2002; 195:151-60.
15. Velazquez L, Cheng A M, Fleming H E, et al. Cytokine signaling and hematopoietic homeostasis are disrupted in Lnk-deficient mice. J Exp Med 2002; 195:1599-611.
16. Tong W, Lodish H F. Lnk inhibits Tpo-mpl signaling and Tpo-mediated megakaryocytopoiesis. J Exp Med 2004; 200:569-80.
17. Buza-Vidas N, Antonchuk J, Qian H, et al. Cytokines regulate postnatal hematopoietic stem cell expansion: opposing roles of thrombopoietin and LNK. Genes Dev 2006; 20:2018-23.
18. Gery S, Cao Q, Gueller S, Xing H, Tefferi A, Koeffler HP. Lnk inhibits myeloproliferative disorder-associated JAK2 mutant, JAK2V617F. J Leukoc Biol 2009; 85:957-65.
19. Carpten J D, Faber A L, Horn C, et al. A transforming mutation in the pleckstrin homology domain of AKT1 in cancer. Nature 2007; 448:439-44.

20. Shoji K, Oda K, Nakagawa S, et al. The oncogenic mutation in the pleckstrin homology domain of AKT1 in endometrial carcinomas. Br J Cancer 2009; 101:145-8.
21. Tong W, Zhang J, Lodish H F. Lnk inhibits erythropoiesis and Epo-dependent JAK2 activation and downstream signaling pathways. Blood 2005; 105:4604-12.
22. Takizawa H, Kubo-Akashi C, Nobuhisa I, et al. Enhanced engraftment of hematopoietic stem/progenitor cells by the transient inhibition of an adaptor protein, Lnk. Blood 2006; 107:2968-75.
23. Jamieson C H, Gotlib J, Durocher J A, et al. The JAK2 V617F mutation occurs in hematopoietic stem cells in polycythemia vera and predisposes toward erythroid differentiation. Proc Natl Acad Sci USA 2006; 103:6224-9.
24. Irish J M, Hovland R, Krutzik P O, et al. Single cell profiling of potentiated phospho-protein networks in cancer cells. Cell 2004; 118:217-28.
25. Verstovsek S, Kantarjian H M, Pardanani A D, et al. The JAK inhibitor, INCB018424, demonstrates durable and marked clinical responses in primary myelofibrosis (PMF) and postpolycythemia/essential thrombocythemia myelofibrosis (post PV/ETMF). ASH Annual Meeting Abstracts 2008; 112:1762.
26. Kotecha N, Flores N, Irish J, et al. Single-cell profiling identifies aberrant STAT5 activation in myeloid malignancies with specific clinical and biologic correlates. Cancer Cell 2008; 14:335-43.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of identifying a human subject as having or being predisposed to a hematolymphoid neoplasm or malignancy, comprising:
   (a) obtaining a sample derived from a subject, wherein the sample comprises blood cells and wherein the blood cells do not have a JAK2 V617F mutation;
   (b) determining the sequence of an LNK gene derived from the sample using PCR or sequencing; and
   (c) identifying the subject as having or being predisposed to a hematolymphoid neoplasm or malignancy based on the determination in step (b) that the LNK gene has an E208Q mutation or a mutation consisting of 603 607del-GCGCT and 613C>G.

2. The method of claim 1, wherein the LNK mutation results in an increase in cytokine signaling in a cell as compared to wild type LNK.

3. The method of claim 1, wherein the identifying step comprises comparing the determined LNK sequence to one or more reference LNK sequence, wherein the one or more reference LNK sequence includes one or both of:
   an LNK sequence from a subject known to be predisposed to a hematolymphoid neoplasm or malignancy; and
   an LNK sequence from a subject known not to be predisposed to a hematolymphoid neoplasm or malignancy.

* * * * *

UNITED STATES PATENT AND TRADEMARK OFFICE
CERTIFICATE OF CORRECTION

PATENT NO.       : 8,945,846 B2
APPLICATION NO.  : 13/005455
DATED            : February 3, 2015
INVENTOR(S)      : Jason Robert Gotlib It is certified that error appears in the above-identified patent and that said Letters Patent is hereby corrected as shown below:

In the Specification

Column 1, Line 5 please replace "This invention was made with government support under contracts HV028183 and CA034233 awarded by the National Institutes of Health. The Government has certain rights in this invention" with -- This invention was made with government support under contracts CA034233, HHSN268201000034C and HV028183 awarded by the National Institutes of Health. The Government has certain rights in the invention --

Signed and Sealed this
Twenty-second Day of December, 2015

Michelle K. Lee
*Director of the United States Patent and Trademark Office*

SEQUENCE LISTING

```
<160> NUMBER OF SEQ ID NOS: 27

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1
cggagaggct gctgagac                                                 18

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
ttgcactcgg cctaaaagtt                                               20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
aagaagttcc tgccctggag                                               20

<210> SEQ ID NO 4
<211> LENGTH: 20
<212> TYPE: DNA
<213> ORGANISM: Artificial Sequence
```

```
<220> FEATURE:
<223> OTHER INFORMATION: synthetic oligonucleotide

<400> SEQUENCE: 4
ctggaaagcc atcacacctc                                                    20

<210> SEQ ID NO 5
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 5
aactcaggcc tggctgg                                                       17

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
gggctacctt atgtcctggg                                                    20

<210> SEQ ID NO 7
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 7
ggtgggagac gagcag                                                        16

<210> SEQ ID NO 8
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 8
ctgtgcactc cgagagc                                                       17

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
gtacgctgga acccagactc                                                    20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
gtctgcagca agcctctacc                                                    20
```

-continued

```
<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
actcagccca ggacataagg                                                    20

<210> SEQ ID NO 12
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 12
gcctctaccc tctacccagt g                                                  21

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
gctcatggag tgttcctggt                                                    20

<210> SEQ ID NO 14
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 14
aggtgctgtg ggaggagag                                                     19

<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 15
gctgaaggag gcggtgct                                                      18

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
gctgtccatg gaggcctcgt                                                    20

<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide
```

<400> SEQUENCE: 17
ggaggcggtg ctatagcgt                                                       19

<210> SEQ ID NO 18
<211> LENGTH: 200
<212> TYPE: DNA
<213> ORGANISM: Artificial Sequence
<220> FEATURE:
<223> OTHER INFORMATION: synthetic oligonucleotide

<400> SEQUENCE: 18
ctgcgctaca gcctggccga cgaggcctcc atggacagcg ggcacgctg gcagcgcggg          60 aggctggcgc tgcgccgggc cccgggcccc gatggccccg accgcgtgct ggagctcttc         120
gacccaccca agagttcaag gcccaagcta caagcagctt gctccagcat ccaggaggtc         180
cggtggtgca cacggcttga                                                    200

<210> SEQ ID NO 19
<211> LENGTH: 195
<212> TYPE: DNA
<213> ORGANISM: Artificial Sequence
<220> FEATURE:
<223> OTHER INFORMATION: synthetic oligonucleotide

<400> SEQUENCE: 19
ctacagcgtg gccgacgagg cctccatgga cagcggggca cgctggcagc gcgggaggct         60
ggcgctgcgc cgggcccgg gccccgatgg ccccgaccgc gtgctggagc tcttcgaccc         120
acccaagagt tcaaggccca agctacaagc agcttgctcc agcatccagg aggtccggtg        180
gtgcacacgg cttga                                                         195

<210> SEQ ID NO 20
<211> LENGTH: 200
<212> TYPE: DNA
<213> ORGANISM: Artificial Sequence
<220> FEATURE:
<223> OTHER INFORMATION: synthetic oligonucleotide

<400> SEQUENCE: 20
ctgcgctaca gcctggccga ccaggcctcc atggacagcg ggcacgctg gcagcgcggg          60 aggctggcgc tgcgccgggc cccgggcccc gatggccccg accgcgtgct ggagctcttc         120
gacccaccca agagttcaag gcccaagcta caagcagctt gctccagcat ccaggaggtc         180
cggtggtgca cacggcttga                                                    200

<210> SEQ ID NO 21
<211> LENGTH: 159
<212> TYPE: PRT
<213> ORGANISM: Artificial Sequence
<220> FEATURE:
<223> OTHER INFORMATION: synthetic peptide

<400> SEQUENCE: 21

Ala Ala Pro Gly Thr Pro Gly Glu Ala Ala Glu Thr Pro Ala Arg Pro
 1               5                  10                  15

Gly Leu Ala Lys Lys Phe Leu Pro Trp Ser Leu Ala Arg Glu Pro Pro
            20                  25                  30

Pro Glu Ala Leu Lys Glu Ala Val Leu Arg Tyr Ser Leu Ala Asp Glu
        35                  40                  45

Ala Ser Met Asp Ser Gly Ala Arg Trp Gln Arg Gly Arg Leu Ala Leu

```
                50                  55                  60
Arg Arg Ala Pro Gly Pro Asp Gly Pro Asp Arg Val Leu Glu Leu Phe
 65                  70                  75                  80

Asp Pro Pro Lys Ser Ser Arg Pro Lys Leu Gln Ala Ala Cys Ser Ser
                 85                  90                  95

Ile Gln Glu Val Arg Trp Cys Thr Arg Leu Glu Met Pro Asp Asn Leu
                100                 105                 110

Tyr Thr Phe Val Leu Lys Val Lys Asp Arg Thr Asp Ile Ile Phe Glu
            115                 120                 125

Val Gly Asp Glu Gln Gln Leu Asn Ser Trp Met Ala Glu Leu Ser Glu
        130                 135                 140

Cys Thr Gly Arg Gly Leu Glu Ser Thr Glu Ala Met His Ile Pro
145                 150                 155
```

<210> SEQ ID NO 22
<211> LENGTH: 104
<212> TYPE: PRT
<213> ORGANISM: Artificial Sequence
<220> FEATURE:
<223> OTHER INFORMATION: synthetic peptide

<400> SEQUENCE: 22

```
Ala Ala Pro Gly Thr Pro Gly Glu Ala Ala Glu Thr Pro Ala Arg Pro
  1               5                  10                  15

Gly Leu Ala Lys Lys Phe Leu Pro Trp Ser Leu Ala Arg Glu Pro Pro
                 20                  25                  30

Pro Glu Ala Leu Lys Glu Ala Val Leu Gln Arg Gly Arg Arg Gly Leu
             35                  40                  45

His Gly Gln Arg Gly Thr Leu Ala Ala Arg Glu Ala Gly Ala Ala Pro
         50                  55                  60

Gly Pro Gly Pro Arg Trp Pro Arg Pro Arg Ala Gly Ala Leu Arg Pro
 65                  70                  75                  80

Thr Gln Glu Phe Lys Ala Gln Ala Thr Ser Ser Leu Leu Gln His Pro
                 85                  90                  95

Gly Gly Pro Val Val His Thr Ala
            100
```

<210> SEQ ID NO 23
<211> LENGTH: 159
<212> TYPE: PRT
<213> ORGANISM: Artificial Sequence
<220> FEATURE:
<223> OTHER INFORMATION: synthetic peptide

<400> SEQUENCE: 23

```
Ala Ala Pro Gly Thr Pro Gly Glu Ala Ala Glu Thr Pro Ala Arg Pro
  1               5                  10                  15

Gly Leu Ala Lys Lys Phe Leu Pro Trp Ser Leu Ala Arg Glu Pro Pro
                 20                  25                  30

Pro Glu Ala Leu Lys Glu Ala Val Leu Arg Tyr Ser Leu Ala Asp Gln
             35                  40                  45

Ala Ser Met Asp Ser Gly Ala Arg Trp Gln Arg Gly Arg Leu Ala Leu
         50                  55                  60

Arg Arg Ala Pro Gly Pro Asp Gly Pro Asp Arg Val Leu Glu Leu Phe
 65                  70                  75                  80

Asp Pro Pro Lys Ser Ser Arg Pro Lys Leu Gln Ala Ala Cys Ser Ser
                 85                  90                  95
```

```
Ile Gln Glu Val Arg Trp Cys Thr Arg Leu Glu Met Pro Asp Asn Leu
            100                 105                 110

Tyr Thr Phe Val Leu Lys Val Lys Asp Arg Thr Asp Ile Ile Phe Glu
        115                 120                 125

Val Gly Asp Glu Gln Gln Leu Asn Ser Trp Met Ala Glu Leu Ser Glu
        130                 135                 140

Cys Thr Gly Arg Gly Leu Glu Ser Thr Glu Ala Met His Ile Pro
145                 150                 155

<210> SEQ ID NO 24
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 24
ggtgctacag cgtggcc                                                  17

<210> SEQ ID NO 25
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 25
ggtgctgcgc tacagcctgg cc                                            22

<210> SEQ ID NO 26
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 26
tggccgagga ggcctcc                                                  17

<210> SEQ ID NO 27
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 27
tggccgacga ggcctcc                                                  17
```